US006355477B1

(12) United States Patent
Fischetti et al.

(10) Patent No.: US 6,355,477 B1
(45) Date of Patent: *Mar. 12, 2002

(54) FIBRONECTIN AND FIBRINOGEN BINDING PROTEIN FROM GROUP A STREPTOCOCCI

(75) Inventors: Vincent A. Fischetti, West Hempstead; Claudia Rocha, New York, both of NY (US)

(73) Assignee: The Rockefeller University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/327,536

(22) Filed: Jun. 8, 1999

Related U.S. Application Data

(63) Continuation-in-part of application No. 08/714,402, filed on Sep. 16, 1996, now Pat. No. 5,910,441.

(51) Int. Cl.$^7$ .......................... C12N 15/00; C07H 21/04
(52) U.S. Cl. ..................................... 435/320.1; 536/23.7
(58) Field of Search ....................... 536/23.7; 435/320.1

(56) References Cited

U.S. PATENT DOCUMENTS

| | | |
|---|---|---|
| 4,399,216 A | 8/1983 | Axel et al. |
| 5,416,021 A | 5/1995 | Hook et al. |
| 5,910,441 A * | 6/1999 | Rocha et al. |

OTHER PUBLICATIONS

Hoeoek, M., et al. "Fibronectin Binding Protein" Accession No. A12915 (1994) Abstract.
Hoeoek, M., et al. "Fibronectin Binding Protein" Accession No. A12901 (1994) Abstract.
Jonsson, K. et al., "Two Different Genes Encode Fibronectin Binding Proteins in *Staphylococcus aureus*", *Eur. J. Biochem.* (1991) 202:1041–1048.
Kline, J.B., et al., "Identification of a Fibronectin–Binding Protein (GfbA) in Pathogenic Group G Streptococci" *Infect. Immun.* (1996) 64:2122–2129.
Kreikemeyer, B. et al., "Characterization of a Novel Fibronectin–Binding Surface Protein in Group A Streptococci" *Mol. Microbiol.* (1995) 17:137–145.
Lindgren P. et al., "Two Different Genes Coding for Fibronectin–Binding Proteins from *Streptococcus dysgalactiae*", *Eur. J. Biochem.* (1993) 214:819–827.
McDevitt, D. et al., "Molecular Characterization of the Clumping Factor (fibrinogen receptor) of *Staphylococcus aureus*", *Mol. Microbiol.* (1994) 11:237–248.
Ozeri, V., et al. "A Two–Domain Mechanism for Group A Streptococcal Adherence Through Protein F to the Extracellular Matrix", *EMBO J.* (1996) 15:989–998.

Rakonjac, J. et al., "DNA Sequence of the Serum Opacity Factor of Group A Streptococci: Identification of a Fibronectin–Binding Repeat Domain", *Infect. Immun.* (1995) 63:622–631.
Talay, S.R. et al., "Fibronectin–Binding Protein of *Streptococcus Pyogenes*: Sequence of the Binding Domain Involved in Adherence of Streptococci to Epithelial Cells", *Infection and Immunity* (1992) 60:3837–3844.
Flock, J–I et al. "Cloning and Expression of the Gene for a Fibronectin–Binding Protein from *Staphylococcus aureus*", *EMBO J.* (1987) 6:2351–2357.
Hanski, E. et al. "Protein F, a Fibronectin–binding Protein, is an Adhesin of the group A Streptococcus *Streptococcus pyogenes*", *Proc. Natl. Acad. Sci. USA* (1992) 89:6172–6176.
Hanski, E. et al., "Expression of Protein F, the Fibronectin–Binding Protein of *Streptococcus pyogenes* JRS4, in Heterologous Streptococcal and Enterococcal Strains Promotes Their Adherence to Respiratory Epithelial Cells", *Infect. Immun.* (1992) 60:5119–5125.
Lindgren, P. et al., "Cloning and Expression of Two Different Genes from *Streptococcus dysgalactiae* Encoding Fibronectin Receptors", *J. Biol. Chem.* (1992) 267:1924–1931.
Sela, S. et al. "Protein F: an adhesin of *Streptococcus pyogenes* Binds Fibronectin via Two Distinct Domains", *Mol. Microbiol.* (1993) 10:1049–1055.
Signas, C., et al. "Nucleotide Sequence of the Gene for a Fibronectin–binding Protein from *Staphylococcus aureus*: Use of this Peptide Sequence in the Synthesis of Biologically Active Peptides", *Proc. Natl. Acad. Sci. USA* (1989) 86:699–703.
Jaffe et al. "Protein F2, a Novel Fibronectin–Binding Protein From *Streptococcus Pyogenus*, Possesses Two Binding Domains" *Molecular Biology* vol. 21, No. 2, pp. 373–384 (Jul. 1996).
Courtney et al "DNA Sequence of the Serum Opacity Factor of Group A Streptococci: Identification of a Fibronectin–Binding Repeat Domain" *Infection and Immunity* vol. 62, No. 9, pp. 3937–3946 (Sep. 1994).

\* cited by examiner

*Primary Examiner*—Mark Navarro
(74) *Attorney, Agent, or Firm*—Burns, Doane, Swecker & Mathis, L.L.P.

(57) ABSTRACT

This invention relates to a novel fibrinogen and fibronectin binding protein from group A streptococci, and the DNA encoding the protein. The protein and its DNA are useful in the preparation of compositions for the diagnosis, treatment, and prevention of streptococcal infection.

11 Claims, 6 Drawing Sheets

A: Homology with S. aureus Clumping Factor.
B: Homology with S. aureus Fibronectin-binding Protein B.
C: Homology with S. dysgalactiae Fibronectin-binding Protein B.
C1: Homology with S. aureus Collagen Adhesin Gene.
R: Repeats Region.

```
GTACGTTAAGCGCTTGAAAAAGAAAGAGTTACAGATAATGACATAAAAAACGCCAAAAAA     60

CCATCAAAATAAATACTCTGACCATAAGATGTAGACTTGACAACTGAAAATAGTAAAATA    120
                                -35                    -10
ACTATTTGACAGTTGGCCTGTAGTCTTTAGTTTTGGACATAGGCTGTCGCTTATGAATGT    180

GGAGAGAGAAAATAAATGACACAAAAAAATAGCTATAAGTTAAGCTTCCTGTTATCCCTA    240
  RBS              M  T  Q  K  N  S  Y  K  L  S  F  L  L  S  L    15

ACAGGATTTATTTTAGGTTTATTATTGGTTTTTATAGGATTGTCCGGAGTATCAGTAGGA    300
 T  G  F  I  L  G  L  L  L  V  F  I  G  L  S  G  V  S  V  G      35

CATGCGGAAACAAGAAATGGAGCAAACAAACAAGGATCTTTTGAAATCAAGAAAGTCGAC    360
 H  A  E  T  R  N  G  A  N  K  Q  G  S  F  E  I  K  K  V  D      55

CAAAACAATAAGCCTTTACCGGGAGCAACTTCTTCACTGACATCAAAGGATGGCAAGGGA    420
 Q  N  N  K  P  L  P  G  A  T  S  S  L  T  S  K  D  G  K  G      75

ACATCTGTTCAAAGCTTCACTTCAAATGATAAAGGTATTGTAGATGCTCAAAATCTCCAA    480
 T  S  V  Q  S  F  T  S  N  D  K  G  I  V  D  A  Q  N  L  Q      95

CCAGGGACTTATACCTTAAAAGAAGAAACAGCACCAGATGGTTATGATAAAACCAGCCGG    540
 P  G  T  Y  T  L  K  E  E  T  A  P  D  G  Y  D  K  T  S  R     115

ACTTGGACAGTGACTGTTTATGAGAACGGCTATACCAAGTTGGTTGAAAATCCCTATAAT    600
 T  W  T  V  T  V  Y  E  N  G  Y  T  K  L  V  E  N  P  Y  N     135

GGGGAAATCATCAGTAAAGCAGGGTCAAAAGATGTTAGTAGTTCTTTACAGTTGGAAAAT    660
 G  E  I  I  S  K  A  G  S  K  D  V  S  S  S  L  Q  L  E  N     155

CCCAAAATGTCAGTTGTTTCTAAATATGGGAAAACAGAGGTTAGTAGTGGCGCAGCGGAT    720
 P  K  M  S  V  V  S  K  Y  G  K  T  E  V  S  S  G  A  A  D     175

TTCTACCGCAACCATGCCGCCTATTTTAAAATGTCTTTTGAGTTGAAACAAAAGGATAAA    780
 F  Y  R  N  H  A  A  Y  F  K  M  S  F  E  L  K  Q  K  D  K     195

TCTGAAACAATCAACCCAGGTGATACCTTTGTGTTACAGCTGGATAGACGTCTCAATCCT    840
 S  E  T  I  N  P  G  D  T  F  V  L  Q  L  D  R  R  L  N  P     215

AAAGGTATCAGTCAAGATATCCCTAAAATCATTTACGACAGTGCAAATAGTCCGCTTGCG    900
 K  G  I  S  Q  D  I  P  K  I  I  Y  D  S  A  N  S  P  L  A     235

ATTGGAAAATACCATGCTGAGAACCATCAACTTATCTATACTTTCACAGATTATATTGCG    960
 I  G  K  Y  H  A  E  N  H  Q  L  I  Y  T  F  T  D  Y  I  A     255

GGTTTAGATAAAGTCCAGTTGTCTGCAGAATTGAGCTTATTCCTAGAGAATAAGGAAGTG   1000
 G  L  D  K  V  Q  L  S  A  E  L  S  L  F  L  E  N  K  E  V     275

TTGGAAAATACTAGTATCTCAAATTTTAAGAGTACCATAGGTGGGCAGGAGATCACCTAT   1080
 L  E  N  T  S  I  S  N  F  K  S  T  I  G  G  Q  E  I  T  Y     295

AAAGGAACGGTTAATGTTCTTTATGGAAATGAGAGCACTAAAGAAAGCAATTATATTACT   1140
 K  G  T  V  N  V  L  Y  G  N  E  S  T  K  E  S  N  Y  I  T     315
```

FIG. 3A

```
AATGGATTGAGCAATGTGGGTGGGAGTATTGAAAGCTACAACACCGAAACGGGAGAATTT  1200
 N  G  L  S  N  V  G  G  S  I  E  S  Y  N  T  E  T  G  E  F    335

GTCTGGTATGTTTATGTCAATCCAAACCGTACCAATATTCCTTATGCGACCATGAATTTA  1260
 V  W  Y  V  Y  V  N  P  N  R  T  N  I  P  Y  A  T  M  N  L    355

TGGGGATTTGGAAGGGCTCGTTCAAATACAAGCGACTTAGAAAACGACGCTAATACAAGT  1320
 W  G  F  G  R  A  R  S  N  T  S  D  L  E  N  D  A  N  T  S    375

AGTGCTGAGCTTGGAGAGATTCAGGTCTATGAAGTACCTGAAGGAGAAAAATTACCATCA  1380
 S  A  E  L  G  E  I  Q  V  Y  E  V  P  E  G  E  K  L  P  S    395

AGTTATGGGGTTGATGTTACAAAACTTACTTTAAGAACGGATATCACAGCAGGCCTAGGA  1440
 S  Y  G  V  D  V  T  K  L  T  L  R  T  D  I  T  A  G  L  G    415

AATGGTTTTCAAATGACCAAACGTCAGCGAATTGACTTTGGAAATAATATCCAAAATAAA  1500
 N  G  F  Q  M  T  K  R  Q  R  I  D  F  G  N  N  I  Q  N  K    435

GCATTTATCATCAAAGTAACAGGGAAAACAGACCAATCTGGTAAGCCATTGGTTGTTCAA  1560
 A  F  I  I  K  V  T  G  K  T  D  Q  S  G  K  P  L  V  V  Q    455

TCCAATTTGGCAAGTTTTCGTGGTGCTTCTGAATATGCTGCTTTTACTCCAGTTGGAGGA  1620
 S  N  L  A  S  F  R  G  A  S  E  Y  A  A  F  T  P  V  G  G    475

AATGTCTACTTCCAAAACGAAATTGCCTTGTCTCCTTCTAAGGGTAGTGGTTCTGGGAAA  1680
 N  V  Y  F  Q  N  E  I  A  L  S  P  S  K  G  S  G  S  G  K    495

AGTGAATTTACTAAGCCCTCTATTACAGTAGCAAATCTAAAACGAGTGGCTCAGCTTCGC  1740
 S  E  F  T  K  P  S  I  T  V  A  N  L  K  R  V  A  Q  L  R    515

TTTAAGAAAATGTCAACTGACAATGTGCCATTGCCAGAAGCGGCTTTTGAGCTGCGTTCA  1800
 F  K  K  M  S  T  D  N  V  P  L  P  E  A  A  F  E  L  R  S    535

TCAAATGGTAATAGTCAGAAATTAGAAGCCAGTTCAAACACACAAGGAGAGGTTCACTTT  1860
 S  N  G  N  S  Q  K  L  E  A  S  S  N  T  Q  G  E  V  H  F    555

AAGGACCTGACCTCGGGCACATATGACCTGTATGAAACAAAAGCGCCAAAAGGTTATCAG  1920
 K  D  L  T  S  G  T  Y  D  L  Y  E  T  K  A  P  K  G  Y  Q    575

CAGGTGACAGAGAAATTGGCGACCGTTACTGTTGATACTACCAAACCTGCTGAGGAAATG  1880
 Q  V  T  E  K  L  A  T  V  T  V  D  T  T  K  P  A  E  E  M    595

GTCACTTGGGGAAGCCCACATTCGTCTGTAAAAGTAGAAGCTAACAAAGAAGTCACGATT  2040
 V  T  W  G  S  P  H  S  S  V  K  V  E  A  N  K  E  V  T  I    615

GTCAACCATAAAGAAACCCTTACGTTTTCAGGGAAGAAAATTTGGGAGAATGACAGACCA  2100
 V  N  H  K  E  T  L  T  F  S  G  K  K  I  W  E  N  D  R  P    635

GATCAACGCCCAGCAAAGATTCAAGTGCAACTGTTGCAAAATGGTCAAAAGATGCCTAAC  2160
 D  Q  R  P  A  K  I  Q  V  Q  L  L  Q  N  G  Q  K  M  P  N    655

CAGATTCAAGAAGTAACGAAGGATAACGATTGGTCTTATCACTTCAAAGACTTGCCTAAG  2200
 Q  I  Q  E  V  T  K  D  N  D  W  S  Y  H  F  K  D  L  P  K    675
```

FIG. 3B

```
TACGATGCCAAGAATCAGGAGTATAAGTACTCAGTTGAAGAAGTAAATGTTCCAGACGGC  2280
 Y  D  A  K  N  Q  E  Y  K  Y  S  V  E  E  V  N  V  P  D  G   695

TACAAGGTGTCGTATTTAGGAAATGATATATTTAACACCAGAGAAACAGAATTTGTGTTT  2340
 Y  K  V  S  Y  L  G  N  D  I  F  N  T  R  E  T  E  F  V  F   715

GAACAGAATAACTTTAACCTTGAATTTGGAAATGCTGAAATAAAAGGTCAATCTGGGTCA  2400
 E  Q  N  N  F  N  L  E  F  G  N  A  E  I  K  G  Q  S  G  S   735

AAAATCATTGATGAAGACACGCTAACGTCTTTCAAAGGTAAGAAAATTTGGAAAAATGAT  2460
 K  I  I  D  E  D  T  L  T  S  F  K  G  K  K  I  W  K  N  D   755

ACGGCAGAAAATCGTCCCCAAGCCATTCAAGTGCAGCTTTATGCTGATGGAGTGGCTGTG  2520
 T  A  E  N  R  P  Q  A  I  Q  V  Q  L  Y  A  D  G  V  A  V   775

GAAGGTCAAACCAAATTTATTTCTGGCTCAGGTAATGAGTGGTCATTTGAGTTTAAAAAC  2580
 E  G  Q  T  K  F  I  S  G  S  G  N  E  W  S  F  E  F  K  N   795

TTGAAGAAGTATAATGGAACAGGTAATGACATCATTTACTCAGTTAAAGAAGTAACTGTT  2640
 L  K  K  Y  N  G  T  G  N  D  I  I  Y  S  V  K  E  V  T  V   815

CCAACAGGTTATGATGTGACTTACTCAGCTAATGATATTATTAATACCAAACGTGAGGTT  2700
 P  T  G  Y  D  V  T  Y  S  A  N  D  I  I  N  T  K  R  E  V   835

ATTACACAACAAGGACCGAAACTAGAGATTGAAGAAACGCTTCCGCTAGAATCAGGTGCT  2760
 I  T  Q  Q  G  P  K  L  E  I  E  E  T  L  P  L  E  S  G  A   855

TCAGGCGGTACCACTACTGTCGAAGACTCACGCCCAGTTGATACCTTATCAGGTTTATCA  2820
 S  G  G  T  T  T  V  E  D  S  R  P  V  D  T  L  S  G  L  S   875

AGTGAGCAAGGTCAGTCCGGTGATATGACAATTGAAGAAGATAGTGCTACCCATATTAAA  2880
 S  E  Q  G  Q  S  G  D  M  T  I  E  E  D  S  A  T  H  I  K   895

TTCTCAAAACGTGATATTGACGGCAAAGAGTTAGCTGGTGCAACTATGGAGTTGCGTGAT  2940
 F  S  K  R  D  I  D  G  K  E  L  A  G  A  T  M  E  L  R  D   915

TCATCTGGTAAAACTATTAGTACATGGATTTCAGATGGACAAGTGAAAGATTTCTACCTG  3000
 S  S  G  K  T  I  S  T  W  I  S  D  G  Q  V  K  D  F  Y  L   935

ATGCCAGGAAAATATACATTTGTCGAAACCGCAGCACCAGACGGTTATGAGATAGCAACT  3060
 M  P  G  K  Y  T  F  V  E  T  A  A  P  D  G  Y  E  I  A  T   955

GCTATTACCTTTACAGTTAATGAGCAAGGTCAGGTTACTGTAAATGGCAAAGCAACTAAA  3120
 A  I  T  F  T  V  N  E  Q  G  Q  V  T  V  N  G  K  A  T  K   975

GGTGACACTCATATTGTCATGGTTGATGCTTACAAGCCAACTAAGGGTTCAGGTCAGGTT  3180
 G  D  T  H  I  V  M  V  D  A  Y  K  P  T  K  G  S  G  Q  V   995

ATTGATATTGAAGAAAAGCTTCCAGACGAGCAAGGTCATTCTGGTTCAACTACTGAAATA  3240
 I  D  I  E  E  K  L  P  D  E  Q  G  H  S  G  S  T  T  E  I  1015
       R1
GAAGACAGTAAATCTTCAGACCTTATCATTGGCGGTCAAGGTGAAGTTGTTGACACAACA  3300
 E  D  S  K  S  S  D  L  I  I  G  G  Q  G  E  V  V  D  T  T  1035
                                                          R2
```

FIG. 3C

```
GAAGACACACAAAGTGGTATGACGGGCCATTCTGGCTCAACTACTGAAATAGAAGATAGC 3360
 E   D   T   Q   S   G   M   T   G   H   S   G   S   T   T   E   I   E   D   S  1055

AAGTCTTCAGACGTTATCATTGGTGGTCAGGGGCAGGTTGTCGAGACAACAGAGGATACC 3420
 K   S   S   D   V   I   I   G   G   Q   G   Q   V   V   E   T   T   E   D   T  1075
                                                                R3
CAAACTGGCATGTACGGGGATTCTGGTTGTAAAACGGAAGTCGAAAATACTAAACTAGTA 3480
 Q   T   G   M   Y   G   D   S   G   C   K   T   E   V   E   N   T   K   L   V  1095

CAATCCTTCCACTTTGATAACAAGGAACCAGAAAGTAACTCTGAGATTCCTAAAAAAGAT 3540
 Q   S   F   H   F   D   N   K   E   P   E   S   N   S   E   I   P   K   K   D  1115

AAGCCAAAGAGTAATACTAGTTTACCAGCAACTGGTGAAAACCACCATAATATCTTCTTT 3600
 K   P   K   S   N   T   S   L   P   A   T   G   E   N   H   H   N   I   F   F  1135
                          . . . . . . . . . . . . . . . .
TGGATGGTTACTTCTTGCTCACTTATTAGTAGTGTTTTTGTAATATCACTAAAATCCAAA 3660
 W   M   V   T   S   C   S   L   I   S   S   V   F   V   I   S   L   K   S   K  1155

AAACGCCTATCATCATGTTAAAATAAGCTGTTGGTGAC 3698
 K   R   L   S   S   C   *  1161
```

FIG. 3D

FIBRONECTIN AND FIBRINOGEN BINDING PROTEIN FROM GROUP A STREPTOCOCCI

This application is a continuation-in-part of Ser. No. 08/714,402, filed Sep. 16, 1996, now U.S. Pat. No. 5,910,441.

BACKGROUND OF THE INVENTION

1. Field of the Invention

This invention relates to a novel fibrinogen and fibronectin binding protein from group A streptococci, and the DNA encoding the protein. The protein and its DNA are useful in the preparation of compositions for the diagnosis, treatment, and prevention of streptococcal infection.

2. Description of the Related Art

Among surface proteins of gram-positive bacteria, the fibronectin-binding (Fn-binding) proteins are responsible for adhesion to host epithelial cells (11, 12). Accordingly, Fn-binding proteins may provide the bacterial cell with the means to initiate the infection process (11, 12, 13, 14). Fn-binding proteins have been identified in *Staphylococcus aureus* (3, 11, 16), class I (SOF⁻) *S. pyogenes* (10, 12, 15) and *Streptococcus dysgalactiae* (6,14). Sequence analysis of these proteins revealed that they are large cell surface proteins, with a predicted size range of 73–122 kDa. The domain architecture of these molecules is similar: a divergent N-terminal portion which constitutes up to 80% of their sequence, followed by three to five homologous tandem Fn-binding repeats of from 32 to 43 residues each (3, 6, 12, 15, 16). In at least two cases, protein F from *S. pyogenes* class I and FnBPB from *S. aureus*, a region of approximately 50 residues N terminal to the tandem repeats has also been implicated as essential for maximal Fn-binding activity (3, 15). A putative cell wall-spanning segment is located C terminally to the repeats, followed by a typical gram-positive cell attachment motif.

Group A Streptococci (*Streptococcus pyogenes*) is the etiologic agent for different suppurative infections (e.g., pharyngitis, impetigo, and necrotizing fasciitis) as well as systemic diseases (e.g., scarlet fever, toxic shock-like syndrome), some of which may lead to serious sequelae, such as rheumatic fever and glomerulonephritis. The ability to bind fibronectin has proven to be one of the mechanisms *Streptococcus pyogenes* use for attachment to host cells (5, 8, 10). Since this glycoprotein is present in body fluids, extracellular matrices, and on the surface of mammalian cells, the identification and characterization of new fibronectin-binding proteins is likely to have pathogenic significance.

SUMMARY OF THE INVENTION

Accordingly, a major object of the present invention is to provide a new streptococcal fibronectin and fibrinogen binding protein. The present invention also provides compositions of matter, including pharmaceutical compositions, comprising the fibronectin and fibrinogen binding protein of the present invention. The present invention further provides antibodies to the fibronectin and fibrinogen binding protein of the present invention and methods for assaying the proteins of the present invention in biological samples using those antibodies.

A further object of the present invention is to provide the DNA encoding the fibronectin and fibrinogen binding protein of the present invention. The present invention also provides vectors, including plasmids and viral vectors comprising the DNA of the present invention, methods of transforming cells with the vectors of the present invention, and transformed cells.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

FIGS. 3A–3D. (SEQ ID NOS: 1–2) Complete nucleotide sequence and deduced amino acid sequence of the Sffbp gene. The putative promoters (−35 and −10) and ribosomal binding site (RBS) sequences are indicated. At the C-terminal region the three repeat sequences (R1, R2, and R3) are underlined. The gram-positive surface protein anchor motif (LPXTG) is followed by the hydrophobic domain and charged C-terminus.

DETAILED DESCRIPTION OF THE PREFERRED EMBODIMENTS OF THE INVENTION

Figure 1:
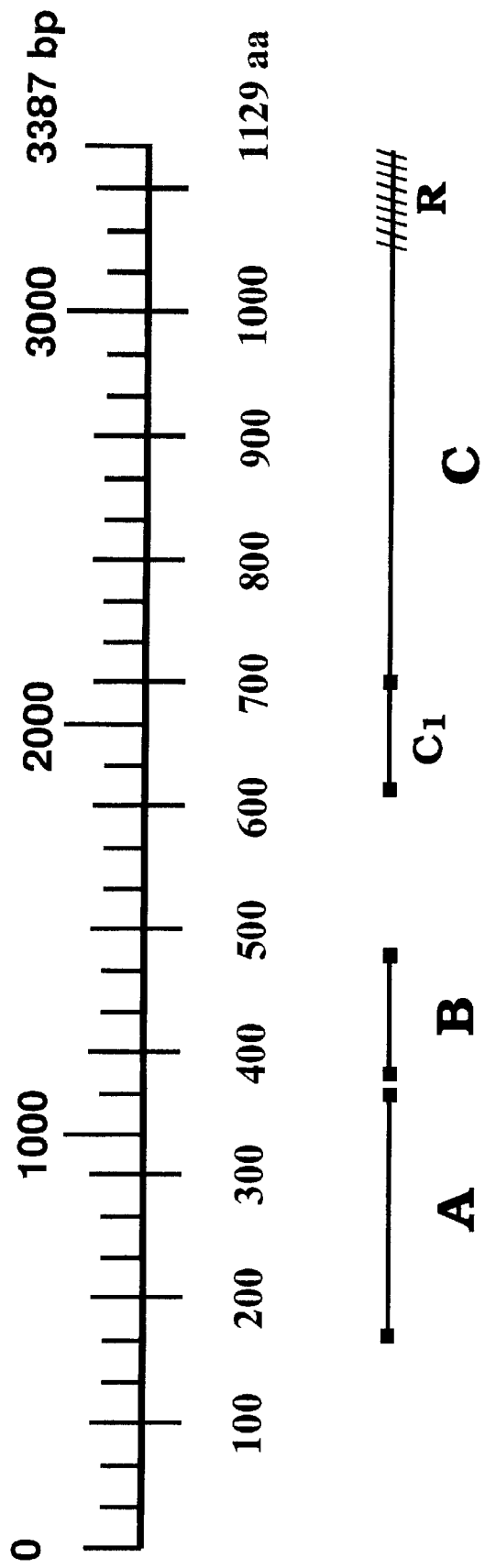
FIG. 1. Map of SFFBP-12 showing the different regions of the protein based on the homology with known fibronectin and fibrinogen binding proteins from streptococci and staphylococci, as well as with the *S. aureus* collagen adhesin gene.

The present invention relates to a fibrinogen- and fibronectin-binding protein (SFFBP-12) of about 123.8 kDa, comprising an amino acid sequence as shown in FIG. 3. The present invention further relates to the gene encoding the SFFBP-12 protein, termed the sffbp-12 gene, comprising the DNA sequence shown in FIG. 3.

More particularly, the present invention relates to methods for detecting and purifying a fibronectin- and fibrinogen-binding protein from group A streptococci, and also relates to the purified fibronectin- and fibrinogen-binding protein itself.

The sffbp-12 gene encoding the SFFBP-12 fibronectin- and fibrinogen-binding protein can also serve as a hybridization probe to isolate corresponding genes from other species by cross-hybridization under low to moderate stringency conditions. Such conditions are usually found empirically by determining the conditions wherein the probe specifically cross-hybridizes to its counterpart gene with a minimum of background hybridization. Nucleic acid hybridization is a well known technique and thoroughly detailed in Sambrook et al.

As noted above, the DNA encoding the fibronectin- and fibrinogen-binding protein can be originally isolated using PCR. Corresponding DNAs from other species can also be isolated using PCR, and oligonucleotides for performing these subsequent PCR reactions can be optimized using the sequence information obtained from DNA cloned from the first species.

A further aspect of the present invention provides the nucleic acids encoding the subject genes in replicable expression vectors and transformed hosts containing these vectors. The replicable expression vectors may also be used to obtain the polypeptides of the present invention by well known methods in recombinant DNA technology.

The instant replicable expression vectors comprise a nucleic acid encoding the subject gene, i.e., the coding sequence is operably linked in proper reading frame to a nucleotide sequence element which directs expression of the protein. In particular, the nucleotide sequence elements may include a promoter, a transcription enhancer element, a termination signal, a translation signal, or a combination of two or more of these elements, generally including at least a promoter element.

Replicable expression vectors are generally DNA molecules engineered for controlled expression of a desired gene, especially where it is desirable to produce large quantities of a particular gene product, or polypeptide. The vectors comprise one or more nucleotide sequences operably linked to a gene to control expression of that gene, the gene being expressed, and an origin of replication which is operable in the contemplated host. Preferably the vector encodes a selectable marker, for example, antibiotic resistance. Replicable expression vectors can be plasmids, bacteriophages, cosmids and viruses. Any expression vector comprising RNA is also contemplated. The replicable expression vectors of this invention can express the protein at high levels. Many of these vectors are based on pBR322, M13 and lambda and are well known in the art and employ such promoters as trp, lac, $P_L$, T7 polymerase and the like. Hence, one skilled in the art has available many choices of replicable expression vectors, compatible hosts, and well-known methods for making and using the vectors.

Moreover, peptides and fragments as well as chemically modified derivatives of the SFFBP-12 protein are also contemplated by the present invention. Briefly, any peptide fragment, derivative or analog which retains substantially the same fibronectin- and fibrinogen-binding activity of the SFFBP-12 protein is contemplated. An analog may be defined herein as a peptide or fragment which exhibits SFFBP-12 protein fibronectin- and/or fibrinogen-binding activity, but has an amino acid substitution, insertion or deletion in comparison to the wild-type protein. Such an analog can be prepared by the "conservative" substitution of an amino acid having similar chemical properties.

Thus, it should also be appreciated that also within the scope of the present invention are DNA sequences encoding an SFFBP-12 protein having the same amino acid sequence as the wild-type protein, but also those DNA sequences which are degenerate to the wild-type sequence. By "degenerate to" is meant that a different three-letter codon is used to specify a particular amino acid. It is well known in the art that the following codons can be used interchangeably to code for each specific amino acid:

| Amino Acid | Codons |
| --- | --- |
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |

-continued

| Amino Acid | Codons |
| --- | --- |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Termination codon | UAA (ochre) or UAG (amber) or UGA (opal) |

It should be understood that the codons specified above are for RNA sequences. The corresponding codons for DNA have T substituted for U.

Mutations can be made in the wild-type sequence such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein.

The following is one example of various groupings of amino acids:

Amino Acids with Nonpolar R Groups

| Alanine | Valine | Leucine | Isoleucine | Proline | Phenylalanine |
| --- | --- | --- | --- | --- | --- |
| | Tryptophan | Methionine | | | |

Amino Acids with Uncharged Polar R Groups

| Glycine | Serine | Threonine | Cysteine | Tyrosine |
| --- | --- | --- | --- | --- |
| Asparagine | Glutamine | | | |

Amino Acids with Charged Polar R Groups (negatively charged at Ph 6.0)

| Aspartic acid | Glutamic acid |
| --- | --- |

Basic Amino Acids (positively charged at pH 6.0)

| Lysine | Arginine | Histidine (at pH 6.0) |
| --- | --- | --- |

Another grouping may be those amino acids with phenyl groups:

| Phenylalanine | Tryptophan | Tyrosine |

Another grouping may be according to molecular weight (i.e., size of R groups):

| Amino Acid | Weight |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (pH 6.0) | 155 |
| Phenylalanine | 165 |
| Arginine | 174 |
| Tyrosine | 181 |
| Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and

G/n for Asn such that a free $NH_2$ can be maintained.

Amino acid substitutions may also be introduced to substitute an amino acid with a particularly preferable property. For example, a Cys may be introduced at a potential site for disulfide bridging with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Purification of the subject SFFBP-12 fibronectin and fibrinogen binding protein from natural or recombinant sources can be accomplished by conventional purification means such as ammonium sulfate precipitation, gel filtration chromatography, ion exchange chromatography, adsorption chromatography, affinity chromatography, chromatofocusing, HPLC, FPLC, and the like. Where appropriate purification steps can be done in batch or in columns.

Peptide fragments of the SFFBP-12 fibronectin and fibrinogen binding protein can be prepared by proteolysis or by chemical degradation. Typical proteolytic enzymes are trypsin, chymotrypsin, V8 protease, subtilisin and the like; the enzymes are commercially available, and protocols for performing proteolytic digests are well known. Peptide fragments are purified by conventional means, as described above. Peptide fragments can often be identified by amino acid composition or sequence. Peptide fragments are useful as immunogens to obtain antibodies against the subject SFFBP-12 fibronectin and fibrinogen binding protein.

The present invention also relates to antibodies to the SFFBP-12 fibronectin and fibrinogen binding protein. Such antibodies may be monoclonal or polyclonal and are contemplated as being useful in developing detection assays (immunoassays) for proteins, monitoring protein levels and in purifying protein. Thus, in accordance with this invention, an antibody to an SFFBP-12 fibronectin and fibrinogen binding protein encompasses monoclonal or polyclonal antibodies to said SFFBP-12 fibronectin and fibrinogen binding protein, or to antigenic parts thereof.

Both polyclonal and monoclonal antibodies to the SFFBP-12 fibronectin and fibrinogen binding protein are obtainable by immunization of an animal with purified SFFBP-12 fibronectin and fibrinogen binding protein, purified recombinant SFFBP-12 fibronectin and fibrinogen binding protein, fragments of these proteins, or purified fusion proteins of SFFBP-12 fibronectin and fibrinogen binding protein with another protein. In the case of monoclonal antibodies, partially purified proteins or fragments may serve as immunogens. The methods of obtaining both types of antibodies are well known in the art with excellent protocols for antibody production being found in Harlow et al. (1988) *Antibodies: A Laboratory Manual*, Cold Spring Harbor Laboratory, Cold Spring Harbor, N.Y., 726 pp.

Polyclonal sera are relatively easily prepared by injection of a suitable laboratory animal with an effective amount of the purified SFFBP-12 fibronectin and fibrinogen binding protein, or parts thereof, collecting serum from the animal, and isolating specific sera by any of the known immunoadsorbent techniques. Antibodies produced by this method are useful in virtually any type of immunoassay.

Monoclonal antibodies are particularly useful because they can be produced in large quantities and with a high degree of homogeneity. Hybridoma cell lines which produce monoclonal antibodies are prepared by fusing an immortal cell line with lymphocytes sensitized against the immunogenic preparation and is done by techniques which are well known to those who are skilled in the art. See, e.g., Douillard, I. Y. and Hoffman, T., "Basic Facts About Hybridomas", in *Compendium of Immunology*, Vol. II, L. Schwartz (Ed.) (1981); Kohler, G. and Milstein, C., *Nature* 256: 495–497 (1975) and *European Journal of Immunology* 6: 511–519 (1976); Harlow et al.; Koprowski, et al., U.S. Pat. No. 4,172,124; Koprowski et al., U.S. Pat. No. 4,196,265 and Wands, U.S. Pat. No. 4,271,145, the teachings of which are herein incorporated by reference.

The presence of the SFFBP-12 fibronectin and fibrinogen binding protein in a sample, such as a culture supernatant and the like, in a microorganism, or in any other source suspected to contain the SFFBP-12 fibronectin and fibrinogen binding protein, can be detected utilizing antibodies prepared as above, either monoclonal or polyclonal, in virtually any type of immunoassay. Likewise, the present antibodies can be used to identify microorganisms which have or produce SFFBP-12 fibronectin and fibrinogen binding protein. Accordingly, the present invention provides a method of detecting an SFFBP-12 fibronectin and fibrinogen binding protein by the steps of contacting a sample suspected of containing said SFFBP-12 fibronectin and fibrinogen binding protein with an antibody of the invention for a time and under conditions sufficient to form an protein-antibody complex and subjecting this complex to a detecting means. As well known to one skilled in the art, the time and conditions for immunodetection assays are variable and depend on the particular assay.

A wide range of detection techniques and conditions are available to one skilled in the art as can be seen by reference to U.S. Pat. Nos. 4,016,043; 4,424,279 and 4,018,653 and to Harlow et al., all of which are incorporated by reference, and which provide extensive protocols for immunodetection of molecules. These techniques, of course, include both single-site and two-site, or "sandwich" assays, assays of the non-competitive types as well as competitive binding assays, ELISA, radioimmunoassays, immunoprecipitation and immunoblotting (Western blotting). Sandwich assays are commonly used, a number of variations of the technique exist, and all are intended to be encompassed by the present invention.

Direct and indirect immunoassays, i.e., ELISA, immunoblotting and the like, may employ reporter molecules linked to either a primary antibody (direct assay) or a second antibody or antibody-specific protein such as Protein A or Protein G (indirect assay). The primary antibody can be an antibody of the subject invention labeled with the desired reporter molecule.

By "reporter molecule," as used herein, is meant a molecule which, by its chemical nature, provides an identifiable signal to detect antigen-antibody complexes. Detection may be either qualitative or quantitative. The most commonly used reporter molecules are either enzymes, fluorophores, or radionuclide containing molecules (i.e., radioisotopes). In the case of an enzyme immunoassay, an enzyme is conjugated to the antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, $\beta$-galactosidase, and alkaline phosphatase among others. The substrate to be used with a particular enzyme is generally chosen for the production of a detectable color change upon reaction. For example, p-nitrophenyl phosphate is suitable for use with alkaline phosphatase conjugates; for peroxidase conjugates, 1,2-phenylenediamine, 5-aminosalicylic acid, or toluidine are commonly used. It is also possible to employ fluorogenic substrates, which yield a fluorescent product rather than the chromogenic substrates noted above. After binding an enzyme-labeled antibody to an antigen or antigen-antibody complex, as appropriate, the excess labeled antibody is washed away, and a solution containing the appropriate substrate is added. The substrate reacts with the enzyme, i.e., the reporter molecule, to give a qualitative visual signal or a quantitative signal which can be assessed to indicate the amount of antigen present in the sample.

Alternately, fluorescent compounds, such as fluorescein and rhodamine, may be chemically coupled to antibodies without altering their binding capacity. As used in immunofluorescence, when activated by illumination with light of a specific wavelength, a fluorophore-labeled antibody absorbs the light energy, inducing the fluorophore into an excited stated which is followed by emission of light having a characteristic wavelength. Generally, the emitted light is a characteristic color in the visible range and is detectable with a light microscope equipped for immunofluorescence. Fluorescent antibodies are used in sandwich assays, direct and indirect immunoassays as described above, except after washing, the immune complex is exposed to light of the appropriate wavelength, and the fluorescence is observed. Immunofluorescence and enzyme-based immunoassay techniques are both well established in the art and are particularly preferred. However, other reporter molecules, such as radioisotopes, chemiluminescent or bioluminescent molecules, may also be employed. It will be readily apparent to the skilled technician how to vary the procedure to suit the required purpose.

Another aspect of the invention provides a means of purifying an SFFBP-12 fibronectin and fibrinogen binding protein by affinity selection. This method involves contacting a sample containing the SFFBP-12 fibronectin and fibrinogen binding protein with an antibody of the invention, and separating the antigen-antibody complex, e.g., the protein-antibody complex from the remainder of the sample and recovering the protein in a form free from the antibody. Typically the complex-containing sample is fractionated and the fraction(s) containing the protein are identified by a convenient biochemical, enzymatic, immunological or other detection means. To facilitate fractionation, the subject antibodies can be bound to a chromatography resin before or after binding to the SFFBP-12 protein. This method can yield purified SFFBP-12 protein in large amounts and in pure form.

Accordingly, the present invention is also directed to a kit for the rapid and convenient assay of an SFFBP-12 fibronectin and fibrinogen binding protein, in samples suspected of containing the SFFBP-12 protein. The kit may contain either an antibody directed to the SFFBP-12 fibronectin and fibrinogen binding protein, and a secondary detectable antibody thereto, or may contain a labeled substrate for the protein, such that a labeled fibronectin- or fibrinogen-SFFBP-12 complex is detected in the presence of the SFFBP-12 protein.

Another aspect of the present invention is directed to a method of detecting the DNA or RNA encoding the subject SFFBP-12 fibronectin and fibrinogen binding protein by nucleic acid hybridization techniques such as Southern blotting, Northern blotting and the like, or by the polymerase chain reaction (PCR). Accordingly, a method of detecting a SFFBP-12 protein is provided which comprises contacting a sample suspected of containing said SFFBP-12 protein-encoding DNA with a first nucleic acid sufficiently complementary to hybridize to a second nucleic acid which encodes said protein in said sample for a time and under conditions sufficient to effect said hybridization and thereby form a complex of said first and second nucleic acids and subjecting said complex to a detecting means. In this method, the first nucleic acid may have a reporter group attached thereto. Reporter groups can include radioisotopes, enzymatically detected groups such as biotin or fluorophores such as rhodamine and fluorescein. Detailed methods for hybridization and blotting is found in Sambrook et al.

For PCR, the present method of detecting a gene encoding the SFFBP-12 fibronectin and fibrinogen binding protein comprises subjecting a sample suspected of containing the SFFBP-12 protein to a polymerase chain reaction (PCR) using at least two oligonucleotide primers sufficiently complementary to hybridize to a nucleic acid in said sample which encodes said SFFBP-12 protein, and thereby producing at least one amplified nucleic acid segment and identifying said segment. PCR has been described in U.S. Pat. Nos. 4,683,195; 4,683,202; and 4,800,159, which are incorporated herein by reference as well as described extensively in the literature, see for example Saiki et al. (1988), *Science* 239: 487–491. The segment may be detected by gel electrophoresis or blotting, for example.

Also encompassed by the present invention are inhibitors of the SFFBP-12 fibronectin and fibrinogen binding protein which can be routinely screened using the assay described above.

A still further part of this invention is a pharmaceutical composition of matter for treating or preventing *Streptococcus sp.* infection with that comprises the SFFBP-12 protein of the present invention or analogs or fragments thereof, mixtures thereof, and/or pharmaceutical salts thereof, and a pharmaceutically-acceptable carrier therefor. Such compositions, when administered to a mammal in need of such treatment, will promote activation of the immune system of the mammal to prevent or ameliorate the effects of streptococcal infection. Such compositions are prepared in accordance with accepted pharmaceutical procedures, for example, as described in *Remington's Pharmaceutical Sciences*, seventeenth edition, ed. Alfonso R. Gennaro, Mack Publishing Company, Easton, Pa. (1985).

For therapeutic use in a method of treating or prevention streptococcal infection, a protein according to the present invention, or its salt, can be conveniently administered in the form of a pharmaceutical composition containing the protein, or its salt, and a pharmaceutically acceptable carrier therefor. Suitable carriers are well known in the art and vary with the desired form and mode of administration of the pharmaceutical composition. For example, they may include diluents or excipients such as fillers, binders, wetting agents, disintegrators, surface-active agents, lubricants, and the like. Typically, the carrier may be a solid, liquid, or vaporizable carrier, or combinations thereof. In one preferred embodiment, the composition is a therapeutic composition and the carrier is a pharmaceutically acceptable carrier.

The compound of the invention or its salt may be formulated together with the carrier into any desired unit dosage form. Typical unit dosage forms include tablets, pills, powders, solutions, suspensions, emulsions, granules, capsules, suppositories; injectable solutions and suspensions are particularly preferred.

Each carrier must be "acceptable" in the sense of being compatible with the other ingredients in the formulation and not injurious to the patient. The carrier must be biologically acceptable and inert, i.e., it must permit the immune system of the mammal receiving the protein to be activated by the protein of the present invention.

The protein of the present invention may be administered for therapy by any suitable routes, including topical, oral, rectal, nasal, vaginal and parenteral (including intraperitoneal, subcutaneous, intramuscular, intravenous, intradermal, and transdermal) routes. It will be appreciated that the preferred route will vary with the condition and age of the patient, the nature of the disorder and the chosen active ingredient including other therapeutic agents. Intranasal, oral, and parenteral routes of administration are preferred. However, other routes may also be utilized depending on the conditions of the patient and how long-lasting the treatment is.

For example, to prepare formulations suitable for injection, solutions and suspensions are sterilized and are preferably isotonic to blood. In making injectable preparations, carriers which are commonly used in this field can also be used, for example, water, ethyl alcohol, propylene glycol, ethoxylated isostearyl alcohol, polyoxylated isostearyl alcohol, polyoxyethylene sorbitol and sorbitate esters. In these instances, adequate amounts of isotonicity adjusters such as sodium chloride, glucose or glycerin can be added to make the preparations isotonic. The aqueous sterile injection solutions may further contain anti-oxidants, buffers, bacteriostats, and like additions acceptable for parenteral formulations.

The formulations may conveniently be presented in unit dosage form and may be prepared by any method known in the art of pharmacy. Such methods include the step of bringing into association the active ingredient with the carrier which may encompass one or more accessory ingredients. In general, the formulations are prepared by uniformly and intimately bringing into association the active ingredient with liquid carriers or finely divided solid carriers or both, and then if necessary shaping the product. Various unit dose and multidose containers, e.g., sealed ampules and vials, may be used, as is well known in the art.

In addition to the ingredients particularly mentioned above, the formulations of this invention may also include other agents conventional in the art for this type of pharmaceutical formulation.

The protein of the invention may be present in the composition in an broad proportion to the carrier. For instance, the compound may be present in the amount of 0.01 to 99.9 wt %, and more preferably in about 0.1 to 99 wt %. Still more preferably, the compound may be present in an amount of about 1 to 70 wt % of the composition.

The dosage of the proteins, pharmaceutically acceptable salts thereof, or mixtures thereof, in the compositions of the invention administered to a patient will vary depending on several factors, including, but not limited to, the age, weight, and species of the patient, the general health of the patient, the severity of the symptoms, whether the composition is being administered alone or in combination with antibiotic agents, the incidence of side effects and the like.

In general, a dose suitable for application in the treatment of streptococcal infection is about 0.001 to 100 mg/kg body weight/dose, preferably about 0.01 to 60 mg/kg body weight/dose, and still more preferably about 0.1 to 40 mg/kg body weight/dose per day. The desired dose may be administered as 1 to 6 or more subdoses administered at appropriate intervals throughout the day. The compounds may be administered repeatedly over a period of months or years, or it may be slowly and constantly infused to the patient. Higher and lower doses may also be administered.

The daily dose may be adjusted taking into account, for example, the above-identified variety of parameters. Typically, the present compositions may be administered in an amount of about 0.001 to 100 mg/kg body weight/day. However, other amounts may also be administered.

To achieve good plasma concentrations, the proteins may be administered, for instance, by intravenous injection of an approximate 0.1 to 1% solution of the active ingredient, optionally in saline, or orally administered as a bolus.

While it is possible for the active ingredient to be administered alone, it is preferably present as a pharmaceutical formulation. The formulations of the present invention comprise at least one active ingredient, as defined above, together with one or more acceptable carriers thereof and optionally other therapeutic agents.

The above method may be practiced by administration of the compounds by themselves or in a combination with other active ingredients, including antibiotic compounds and/or therapeutic agents in a pharmaceutical composition. Other therapeutic agents suitable for use herein are any compatible drugs that are effective by the same or other mechanisms for the intended purpose, or drugs that are complementary to those of the present agents. These include agents that are effective for the treatment of streptococcal infections and/or associated conditions in humans.

The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained. The therapeutic method of the invention may be used in conjunction with other therapies as determined by the practitioner.

The following examples are presented in order to more fully illustrate the preferred embodiments of the invention.

They should in no way be construed, however, as limiting the broad scope of the invention.

EXAMPLE 1

Identification and Characterization of SFFBP-12 Protein and Corresponding sffbp-12 DNA.

A genomic library from an M12 strain was screened using a mono-specific rabbit antiserum against the cell-wall-associated region of the streptococcal M protein. Using this strategy, a gene was identified, which was termed streptococcal fibronectin-fibrinogen binding protein (sffbp-12). The gene encodes a protein (SFFBP-12) of about 123.8 kDa, making it one of the largest proteins of its kind identified for group A streptococci. The translated sequence of sffbp-12 has at the N-terminus a stretch of about 30 hydrophobic amino acids, which may represent a leader peptide. The sequence of the mature protein can be divided into three different regions (A, B, and C) depending on the homology shared with fibronectin-fibrinogen binding proteins previously described in Group A, C, and G streptococci, as well as S. aureus. Region C and the repeated region at the C-terminal end of the molecule exhibit high amino acid sequence identity (69% and 67–75% respectively) with the fibronectin binding protein (FnBB) from S. dysgalactiae (6). N-terminal regions A and B exhibit lower but significant identity (21%) with the fibronectin binding protein (3) and fibrinogen binding protein (clumping factor) from S. aureus (7), respectively (FIG. 1, Table 1). The protein also exhibits the C-terminal LPXTGX motif typical of surface proteins on gram-positive bacteria.

RNA Transcription

Figure 2:
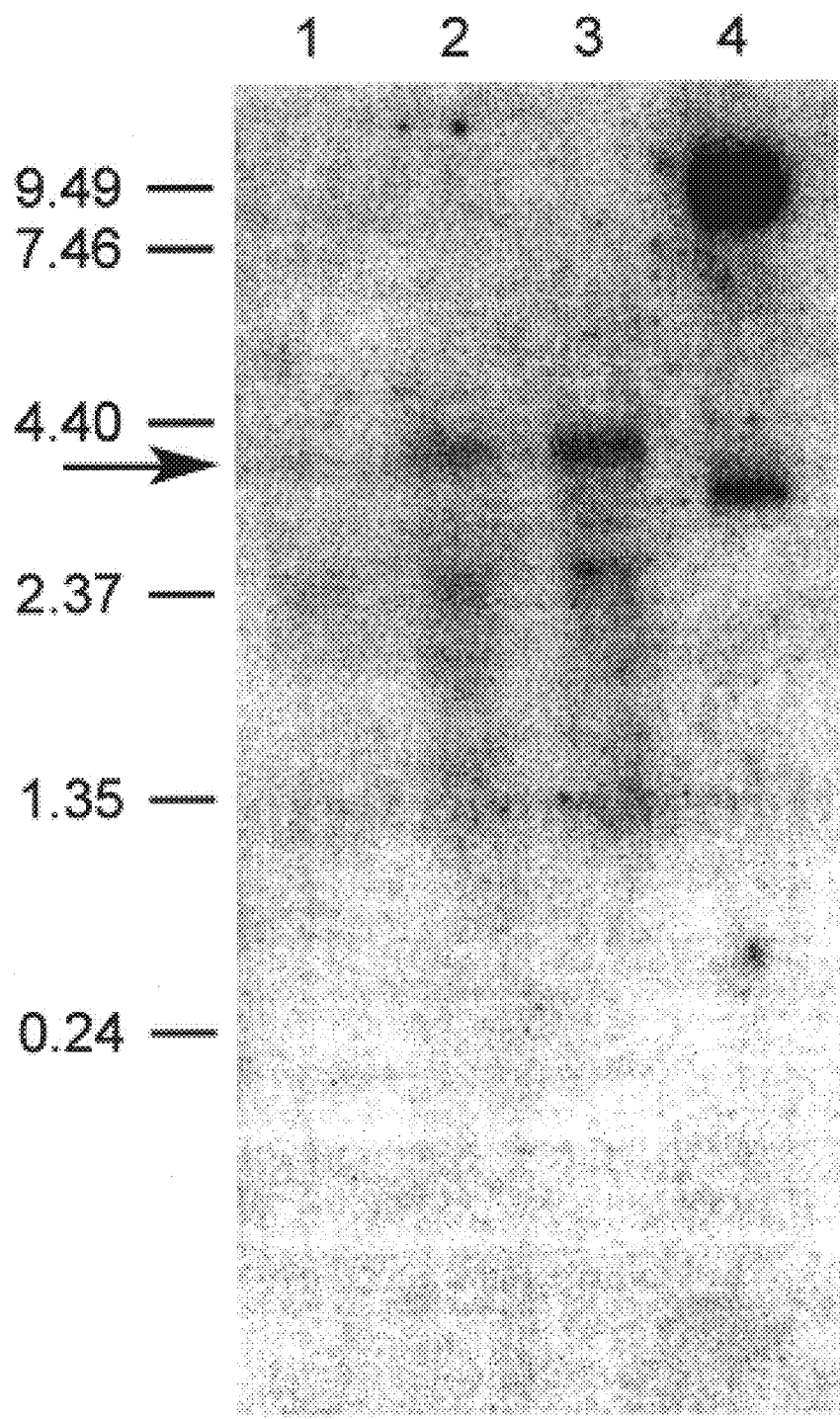
FIG. 2. Northern hybridization with a specific probe for sffbp-12. 10 μg of total RNA was loaded from each sample (1–3), and 5 ng of the control DNA (4). The hybridization solution contained 1×10⁶ cpm/ml of the ³²P-labeled probe. Lanes: 1) 3 hr culture; 2) 4 hour culture; 3) 5 hr culture; 4) Control: plasmid pBS3.1Q containing the C-terminal half of sffbp-12. The positions of the RNA molecular markers (in kilobases) are shown to the left.

To determine if sffbp-12 is in fact transcribed, and at what stage during the growth cycle maximal transcription occurred, a Northern blot was performed on total RNA isolated at different times in the growth cycle (FIG. 2). Hybridization of the blot with a probe specific for the sffbp-12 sequence revealed a band (at 4 and 5 hr of growth) of 3.7 Kb, the expected size of the complete sffbp-12 transcript.

TABLE 1

Homologies of SFFBP-12 With Reported Fibronectin and Fibrinogen Binding Proteins

| | SFFBP-12 | | | | |
|---|---|---|---|---|---|
| | A | B | C | C1 | R |
| S. dysgalactiae Fibronectin-binding protein FnBB (6) | | | 69% | | 67–75%[a] |
| S. aureus Fibronectin binding protein B (3) | | 21% | | | |
| S. equisimilis Fibronectin binding protein | | | 65% | | 50–60%[e] |
| S. aureus Fibronectin binding protein (PSDF 203) | | | 41% | | 61%[c] |
| S. aureus Fibronectin binding protein | | | 59% | | |
| S. dysgalactie Fibronectin binding protein FnBA | | | 38% | | 70%[c] |
| S. pyogenes Serum Opacity factor (SOF) | | | 45% | | 48%[d] |
| S. pyogenes Fibronectin binding protein II. SfbII | | | 45% | | 48%[d] |
| S. pyogenes Fibronectin binding protein II. Sfb (Fn binding domain) | | | 48% | | 48%[b] |
| S. pyogenes Protein F | | | 47% | | 47%[b] |
| Group G Streptococcus Fibronectin-binding protein GfbA | | | 47% | | 47%[b] |
| S. aureus Collagen adhesin | | | | 63% | |
| S. aureus Fibrinogen-binding protein. Clumping factor (7) | | 21% | | | | a: Repeat regions;
b: R1 and R2 repeats;
c: Half R2 to beginning R3 repeats;
d: Part of R3 repeat;
e: R1 repeat

Summary/Conclusions

Fibronectin and fibrinogen-binding proteins have been described as possible adhesin in streptococci and staphylococci. Recent published data have demonstrated that Protein F, a fibronectin-binding protien from group A streptococci, is important in adherence to respiratory cells (8). Other similar proteins already described (i.e., SOF, Sfb and SfbII) are able to competitively inhibit the binding of fibronectin to S. pyogenes (5, 9, 10). Similarly, clumping factor from S. aureus is known to promote adherence to fibrinogen-coated surfaces (7). When the sequence from SFFBP-12 was compared against all other fibronectin and fibrinogen-binding proteins described in streptococci and staphylococci (1–10), an identity at the amino acid level ranging from 38% to 69% was found for the C region. For the repeated region (R), the identity ranged between 47% and 75%. Unlike all the other proteins already described in group A streptococci, the protein of the present invention, SFFBP-12, shares a high degree of homology (67–75%) with the fibronectin-binding protein B from S. dysgalactiae (6) as well as homology with the S. aureus clumping factor (7) and fibronectin-binding protein B(3), making it a new potential fibronectin-fibrinogen binding protein for group A streptococci. These characteristics would also imply that SFFBP-12 contains two different fibronectin-binding domains, thus enhancing its role as a possible major adhesin molecule. RNA transcription assays showed a transcript with the expected molecular size for the intact SFFBP-12 protein, confirming that the protein is actively expressed during bacterial growth. SFFBP-12 is the largest protein of its kind identified from group A streptococci and is comparable in size to the fibronectin binding protein B from S. dysgalactiae (6). If it is shown that SFFBP-12 does in fact bind both fibronectin and fibrinogen, as the sequence data suggest, it would make this molecule a major virulence determinant for the group A streptococcus.

EXAMPLE 2

Determination of Fibronectin Binding Activity

The method described in Rakonjac, J. V. et al. Infect. Immun. 63:622–631 (1995) is useful to assay fibronectin binding activity. Briefly, recombinant SFFBP-12 protein is prepared from whole-cell lysates of cells transformed with sffbp-12, separated by SDS-PAGE, and electroblotted to nitrocellulose. The blots are then blocked by incubation in 10 mM HEPES (N-2-hydroxyethyl-piperazine-N'-2- ethanesulfonic acid) buffer, containing 150 mM NaCl, 10 mM $MgCl_2$, 2 mM $CaCl_2$, 60 mM KCl, 0.5% Tween 20, 0.04% $NaN_3$, and 0.5% bovine serum albumin, pH 7.4, for 2 to 3 h at room temperature. Subsequently, blots are then probed for 3 to 4 h at room temperature in the same buffer containing $^{125}$I-fibronectin adjusted to $3\times10^5$ cpm/ml. Blots are then washed three times with blocking buffer, dried, and exposed to Kodak Blue Brand® film in the presence of an intensifying screen for 24 to 36 h at −70° C.

Radioiodination of fibronectin may be achieved be using Iodobeads® (Pierce Chemical Co., Rockford, Ill.). The labeled protein is separated from free iodine by filtration through Sephadex G-25 (PD-10; Pharmacia LKB Biotechnology, Inc.) and equilibrated in 100 mM phosphate-buffered saline, pH 6.5. The specific activity of the iodinated fibronectin will be approximately $5\times10^5$ cpm/pg.

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

REFERENCES

The following scientific journal articles illustrate the state of the art, and are incorporated herein by reference:
1. Hoeoek, M., et al. *Accession No.* A12915
2. Hoeoek, M., et al. *Accession No.* A12901.
3. Jonsson, K. et al., *Eur J. Biochem.* 202:1041–1048 (1991).
4. Kline, J. B. et al., *Infect. Immun.* 64:2122–2129 (1996).
5. Kreikemeyer, B., et al., *Mol. Microbiol.* 17:137–145 (1995).
6. Lindgren, P. et al., *Eur. J. Biochem.* 214:819–827 (1993).
7. McDevitt, D., et al. *Mol. Microbiol*/1:237–248 (1994).
8. Ozeri, V., et al. *EMBO J.* 15:989–998 (1996).
9. Rakonjac, J. V. et al. *Infect. Immun.* 63:622–631 (1995).
10. Talay, S. R. et al. *Infect. Immun.* 60:3837–3844 (1992).
11. Flock, J.-l. et al. *EMBO J.* 6:2351–2357 (1987).
12. Hanski, E. et al. *Proc. Natl. Acad. Sci. USA* 89:6271–6176 (1992).
13. Hanski, E. et al. *Infect. Immun.* 60:5119–5125 (1992).
14. Lindgren, P. et al. *J. Biol. Chem.* 267:1924–1931 (1992).
15. Sela, S. et al. *Mol. Microbiol.* 10:1049–1055 (1993).
16. Signas, C. et al. *Proc. Natl. Acad. Sci. USA* 86:699–703 (1989).

What is claimed is:

1. A purified DNA fragment encoding the Streptococcal fibrinogen and fibronectin binding protein (SFFBP-12) (SEQ ID NO: 2).

2. A DNA according to claim 1, wherein the DNA comprises the sequence of the sffbp-12 gene (SEQ ID NO: 1).

3. A replicable expression vector comprising the DNA of claim 1.

4. An isolated host cell transformed with the vector of claim 3.

5. A DNA according to claim 1, operably linked to one or more elements selected from the group consisting of a promoter, a transcription enhancer element, a termination signal, a translation signal, and a combination of two or more of these elements.

6. A DNA according to claim 5, further comprising a selectable marker.

7. A DNA according to claim 1, wherein the DNA consists of the sequence of the sffbp-12 gene (SEQ ID NO: 1).

8. A replicable expression vector comprising the DNA of claim 7.

9. An isolated host cell transformed with the vector of claim 8.

10. A DNA according to claim 8, further comprising one or more elements selected from the group consisting of a promoter, a transcription enhancer element, a termination signal, a translation signal, and a combination of two or more of these elements.

11. A DNA according to claim 10, further comprising a selectable marker.

* * * * *

SEQUENCE LISTING

```
<160> NUMBER OF SEQ ID NOS:  2

<210> SEQ ID NO 1
<211> LENGTH: 3698
<212> TYPE: DNA
<213> ORGANISM: SFFBP gene
<220> FEATURE:
<221> NAME/KEY: CDS
<222> LOCATION: (196)..(3681)

<400> SEQUENCE: 1
gtacgttaag cgcttgaaaa agaaagagtt acagataatg acataaaaaa cgccaaaaaa        60
ccatcaaaat aaatactctg accataagat gtagacttga caactgaaaa tagtaaaata       120
actatttgac agttggcctg tagtctttag ttttggacat aggctgtcgc ttatgaatgt       180
ggagagagaa aataa atg aca caa aaa aat agc tat aag tta agc ttc ctg       231
                 Met Thr Gln Lys Asn Ser Tyr Lys Leu Ser Phe Leu
                  1               5                  10 tta tcc cta aca gga ttt att tta ggt tta tta ttg gtt ttt ata gga        279
Leu Ser Leu Thr Gly Phe Ile Leu Gly Leu Leu Leu Val Phe Ile Gly
             15                  20                  25 ttg tcc gga gta tca gta gga cat gcg gaa aca aga aat gga gca aac        327
Leu Ser Gly Val Ser Val Gly His Ala Glu Thr Arg Asn Gly Ala Asn
         30                  35                  40 aaa caa gga tct ttt gaa atc aag aaa gtc gac caa aac aat aag cct        375
Lys Gln Gly Ser Phe Glu Ile Lys Lys Val Asp Gln Asn Asn Lys Pro
 45                  50                  55                  60 tta ccg gga gca act tct tca ctg aca tca aag gat ggc aag gga aca        423
Leu Pro Gly Ala Thr Ser Ser Leu Thr Ser Lys Asp Gly Lys Gly Thr
                 65                  70                  75 tct gtt caa agc ttc act tca aat gat aaa ggt att gta gat gct caa        471
Ser Val Gln Ser Phe Thr Ser Asn Asp Lys Gly Ile Val Asp Ala Gln
             80                  85                  90 aat ctc caa cca ggg act tat acc tta aaa gaa gaa aca gca cca gat        519
Asn Leu Gln Pro Gly Thr Tyr Thr Leu Lys Glu Glu Thr Ala Pro Asp
         95                 100                 105
```

```
ggt tat gat aaa acc agc cgg act tgg aca gtg act gtt tat gag aac         567
Gly Tyr Asp Lys Thr Ser Arg Thr Trp Thr Val Thr Val Tyr Glu Asn
    110                 115                 120 ggc tat acc aag ttg gtt gaa aat ccc tat aat ggg gaa atc atc agt         615
Gly Tyr Thr Lys Leu Val Glu Asn Pro Tyr Asn Gly Glu Ile Ile Ser
125                 130                 135                 140 aaa gca ggg tca aaa gat gtt agt agt tct tta cag ttg gaa aat ccc         663
Lys Ala Gly Ser Lys Asp Val Ser Ser Ser Leu Gln Leu Glu Asn Pro
                145                 150                 155 aaa atg tca gtt gtt tct aaa tat ggg aaa aca gag gtt agt agt ggc         711
Lys Met Ser Val Val Ser Lys Tyr Gly Lys Thr Glu Val Ser Ser Gly
                160                 165                 170 gca gcg gat ttc tac cgc aac cat gcc gcc tat ttt aaa atg tct ttt         759
Ala Ala Asp Phe Tyr Arg Asn His Ala Ala Tyr Phe Lys Met Ser Phe
                175                 180                 185 gag ttg aaa caa aag gat aaa tct gaa aca atc aac cca ggt gat acc         807
Glu Leu Lys Gln Lys Asp Lys Ser Glu Thr Ile Asn Pro Gly Asp Thr
        190                 195                 200 ttt gtg tta cag ctg gat aga cgt ctc aat cct aaa ggt atc agt caa         855
Phe Val Leu Gln Leu Asp Arg Arg Leu Asn Pro Lys Gly Ile Ser Gln
205                 210                 215                 220 gat atc cct aaa atc att tac gac agt gca aat agt ccg ctt gcg att         903
Asp Ile Pro Lys Ile Ile Tyr Asp Ser Ala Asn Ser Pro Leu Ala Ile
                225                 230                 235 gga aaa tac cat gct gag aac cat caa ctt atc tat act ttc aca gat         951
Gly Lys Tyr His Ala Glu Asn His Gln Leu Ile Tyr Thr Phe Thr Asp
                240                 245                 250 tat att gcg ggt tta gat aaa gtc cag ttg tct gca gaa ttg agc tta         999
Tyr Ile Ala Gly Leu Asp Lys Val Gln Leu Ser Ala Glu Leu Ser Leu
        255                 260                 265 ttc cta gag aat aag gaa gtg ttg gaa aat act agt atc tca aat ttt        1047
Phe Leu Glu Asn Lys Glu Val Leu Glu Asn Thr Ser Ile Ser Asn Phe
270                 275                 280 aag agt acc ata ggt ggg cag gag atc acc tat aaa gga acg gtt aat        1095
Lys Ser Thr Ile Gly Gly Gln Glu Ile Thr Tyr Lys Gly Thr Val Asn
285                 290                 295                 300 gtt ctt tat gga aat gag agc act aaa gaa agc aat tat att act aat        1143
Val Leu Tyr Gly Asn Glu Ser Thr Lys Glu Ser Asn Tyr Ile Thr Asn
                305                 310                 315 gga ttg agc aat gtg ggt ggg agt att gaa agc tac aac acc gaa acg        1191
Gly Leu Ser Asn Val Gly Gly Ser Ile Glu Ser Tyr Asn Thr Glu Thr
        320                 325                 330 gga gaa ttt gtc tgg tat gtt tat gtc aat cca aac cgt acc aat att        1239
Gly Glu Phe Val Trp Tyr Val Tyr Val Asn Pro Asn Arg Thr Asn Ile
            335                 340                 345 cct tat gcg acc atg aat tta tgg gga ttt gga agg gct cgt tca aat        1287
Pro Tyr Ala Thr Met Asn Leu Trp Gly Phe Gly Arg Ala Arg Ser Asn
350                 355                 360 aca agc gac tta gaa aac gac gct aat aca agt agt gct gag ctt gga        1335
Thr Ser Asp Leu Glu Asn Asp Ala Asn Thr Ser Ser Ala Glu Leu Gly
365                 370                 375                 380 gag att cag gtc tat gaa gta cct gaa gga gaa aaa tta cca tca agt        1383
Glu Ile Gln Val Tyr Glu Val Pro Glu Gly Glu Lys Leu Pro Ser Ser
                385                 390                 395 tat ggg gtt gat gtt aca aaa ctt act tta aga acg gat atc aca gca        1431
Tyr Gly Val Asp Val Thr Lys Leu Thr Leu Arg Thr Asp Ile Thr Ala
                400                 405                 410 ggc cta gga aat ggt ttt caa atg acc aaa cgt cag cga att gac ttt        1479
Gly Leu Gly Asn Gly Phe Gln Met Thr Lys Arg Gln Arg Ile Asp Phe
        415                 420                 425
```

```
gga aat aat atc caa aat aaa gca ttt atc atc aaa gta aca ggg aaa       1527
Gly Asn Asn Ile Gln Asn Lys Ala Phe Ile Ile Lys Val Thr Gly Lys
        430                 435                 440 aca gac caa tct ggt aag cca ttg gtt gtt caa tcc aat ttg gca agt       1575
Thr Asp Gln Ser Gly Lys Pro Leu Val Val Gln Ser Asn Leu Ala Ser
445                 450                 455                 460 ttt cgt ggt gct tct gaa tat gct gct ttt act cca gtt gga gga aat       1623
Phe Arg Gly Ala Ser Glu Tyr Ala Ala Phe Thr Pro Val Gly Gly Asn
                465                 470                 475 gtc tac ttc caa aac gaa att gcc ttg tct cct tct aag ggt agt ggt       1671
Val Tyr Phe Gln Asn Glu Ile Ala Leu Ser Pro Ser Lys Gly Ser Gly
            480                 485                 490 tct ggg aaa agt gaa ttt act aag ccc tct att aca gta gca aat cta       1719
Ser Gly Lys Ser Glu Phe Thr Lys Pro Ser Ile Thr Val Ala Asn Leu
        495                 500                 505 aaa cga gtg gct cag ctt cgc ttt aag aaa atg tca act gac aat gtg       1767
Lys Arg Val Ala Gln Leu Arg Phe Lys Lys Met Ser Thr Asp Asn Val
    510                 515                 520 cca ttg cca gaa gcg gct ttt gag ctg cgt tca tca aat ggt aat agt       1815
Pro Leu Pro Glu Ala Ala Phe Glu Leu Arg Ser Ser Asn Gly Asn Ser
525                 530                 535                 540 cag aaa tta gaa gcc agt tca aac aca caa gga gag gtt cac ttt aag       1863
Gln Lys Leu Glu Ala Ser Ser Asn Thr Gln Gly Glu Val His Phe Lys
                545                 550                 555 gac ctg acc tcg ggc aca tat gac ctg tat gaa aca aaa gcg cca aaa       1911
Asp Leu Thr Ser Gly Thr Tyr Asp Leu Tyr Glu Thr Lys Ala Pro Lys
            560                 565                 570 ggt tat cag cag gtg aca gag aaa ttg gcg acc gtt act gtt gat act       1959
Gly Tyr Gln Gln Val Thr Glu Lys Leu Ala Thr Val Thr Val Asp Thr
        575                 580                 585 acc aaa cct gct gag gaa atg gtc act tgg gga agc cca cat tcg tct       2007
Thr Lys Pro Ala Glu Glu Met Val Thr Trp Gly Ser Pro His Ser Ser
    590                 595                 600 gta aaa gta gaa gct aac aaa gaa gtc acg att gtc aac cat aaa gaa       2055
Val Lys Val Glu Ala Asn Lys Glu Val Thr Ile Val Asn His Lys Glu
605                 610                 615                 620 acc ctt acg ttt tca ggg aag aaa att tgg gag aat gac aga cca gat       2103
Thr Leu Thr Phe Ser Gly Lys Lys Ile Trp Glu Asn Asp Arg Pro Asp
                625                 630                 635 caa cgc cca gca aag att caa gtg caa ctg ttg caa aat ggt caa aag       2151
Gln Arg Pro Ala Lys Ile Gln Val Gln Leu Leu Gln Asn Gly Gln Lys
            640                 645                 650 atg cct aac cag att caa gaa gta acg aag gat aac gat tgg tct tat       2199
Met Pro Asn Gln Ile Gln Glu Val Thr Lys Asp Asn Asp Trp Ser Tyr
        655                 660                 665 cac ttc aaa gac ttg cct aag tac gat gcc aag aat cag gag tat aag       2247
His Phe Lys Asp Leu Pro Lys Tyr Asp Ala Lys Asn Gln Glu Tyr Lys
    670                 675                 680 tac tca gtt gaa gaa gta aat gtt cca gac ggc tac aag gtg tcg tat       2295
Tyr Ser Val Glu Glu Val Asn Val Pro Asp Gly Tyr Lys Val Ser Tyr
685                 690                 695                 700 tta gga aat gat ata ttt aac acc aga gaa aca gaa ttt gtg ttt gaa       2343
Leu Gly Asn Asp Ile Phe Asn Thr Arg Glu Thr Glu Phe Val Phe Glu
                705                 710                 715 cag aat aac ttt aac ctt gaa ttt gga aat gct gaa ata aaa ggt caa       2391
Gln Asn Asn Phe Asn Leu Glu Phe Gly Asn Ala Glu Ile Lys Gly Gln
            720                 725                 730 tct ggg tca aaa atc att gat gaa gac acg cta acg tct ttc aaa ggt       2439
Ser Gly Ser Lys Ile Ile Asp Glu Asp Thr Leu Thr Ser Phe Lys Gly
```

-continued

|     |     | 735 |     |     |     | 740 |     |     |     | 745 |     |     |      |
|-----|-----|-----|-----|-----|-----|-----|-----|-----|-----|-----|-----|-----|------|
| aag | aaa | att | tgg | aaa | aat | gat | acg | gca | gaa | aat | cgt | ccc | caa | gcc | att | 2487 |
| Lys | Lys | Ile | Trp | Lys | Asn | Asp | Thr | Ala | Glu | Asn | Arg | Pro | Gln | Ala | Ile |      |
|     | 750 |     |     |     | 755 |     |     |     | 760 |     |     |     |     |     |     |      | caa gtg cag ctt tat gct gat gga gtg gct gtg gaa ggt caa acc aaa   2535
Gln Val Gln Leu Tyr Ala Asp Gly Val Ala Val Glu Gly Gln Thr Lys
765             770                 775                 780 ttt att tct ggc tca ggt aat gag tgg tca ttt gag ttt aaa aac ttg   2583
Phe Ile Ser Gly Ser Gly Asn Glu Trp Ser Phe Glu Phe Lys Asn Leu
                785                 790                 795 aag aag tat aat gga aca ggt aat gac atc att tac tca gtt aaa gaa   2631
Lys Lys Tyr Asn Gly Thr Gly Asn Asp Ile Ile Tyr Ser Val Lys Glu
                    800                 805                 810 gta act gtt cca aca ggt tat gat gtg act tac tca gct aat gat att   2679
Val Thr Val Pro Thr Gly Tyr Asp Val Thr Tyr Ser Ala Asn Asp Ile
                815                 820                 825 att aat acc aaa cgt gag gtt att aca caa caa gga ccg aaa cta gag   2727
Ile Asn Thr Lys Arg Glu Val Ile Thr Gln Gln Gly Pro Lys Leu Glu
            830                 835                 840 att gaa gaa acg ctt ccg cta gaa tca ggt gct tca ggc ggt acc act   2775
Ile Glu Glu Thr Leu Pro Leu Glu Ser Gly Ala Ser Gly Gly Thr Thr
845                 850                 855                 860 act gtc gaa gac tca cgc cca gtt gat acc tta tca ggt tta tca agt   2823
Thr Val Glu Asp Ser Arg Pro Val Asp Thr Leu Ser Gly Leu Ser Ser
                    865                 870                 875 gag caa ggt cag tcc ggt gat atg aca att gaa gaa gat agt gct acc   2871
Glu Gln Gly Gln Ser Gly Asp Met Thr Ile Glu Glu Asp Ser Ala Thr
                880                 885                 890 cat att aaa ttc tca aaa cgt gat att gac ggc aaa gag tta gct ggt   2919
His Ile Lys Phe Ser Lys Arg Asp Ile Asp Gly Lys Glu Leu Ala Gly
            895                 900                 905 gca act atg gag ttg cgt gat tca tct ggt aaa act att agt aca tgg   2967
Ala Thr Met Glu Leu Arg Asp Ser Ser Gly Lys Thr Ile Ser Thr Trp
910                 915                 920 att tca gat gga caa gtg aaa gat ttc tac ctg atg cca gga aaa tat   3015
Ile Ser Asp Gly Gln Val Lys Asp Phe Tyr Leu Met Pro Gly Lys Tyr
925                 930                 935                 940 aca ttt gtc gaa acc gca gca cca gac ggt tat gag ata gca act gct   3063
Thr Phe Val Glu Thr Ala Ala Pro Asp Gly Tyr Glu Ile Ala Thr Ala
                945                 950                 955 att acc ttt aca gtt aat gag caa ggt cag gtt act gta aat ggc aaa   3111
Ile Thr Phe Thr Val Asn Glu Gln Gly Gln Val Thr Val Asn Gly Lys
            960                 965                 970 gca act aaa ggt gac act cat att gtc atg gtt gat gct tac aag cca   3159
Ala Thr Lys Gly Asp Thr His Ile Val Met Val Asp Ala Tyr Lys Pro
        975                 980                 985 act aag ggt tca ggt cag gtt att gat att gaa gaa aag ctt cca gac   3207
Thr Lys Gly Ser Gly Gln Val Ile Asp Ile Glu Glu Lys Leu Pro Asp
    990                 995                 1000 gag caa ggt cat tct ggt tca act act gaa ata gaa gac agt aaa tct   3255
Glu Gln Gly His Ser Gly Ser Thr Thr Glu Ile Glu Asp Ser Lys Ser
1005                1010                1015                1020 tca gac ctt atc att ggc ggt caa ggt gaa gtt gtt gac aca aca gaa   3303
Ser Asp Leu Ile Ile Gly Gly Gln Gly Glu Val Val Asp Thr Thr Glu
                1025                1030                1035 gac aca caa agt ggt atg acg ggc cat tct ggc tca act act gaa ata   3351
Asp Thr Gln Ser Gly Met Thr Gly His Ser Gly Ser Thr Thr Glu Ile
            1040                1045                1050 gaa gat agc aag tct tca gac gtt atc att ggt ggt cag ggg cag gtt   3399

```
                                                                              -continued Glu Asp Ser Lys Ser Asp Val Ile Ile Gly Gly Gln Gly Gln Val
         1055                1060                1065 gtc gag aca aca gag gat acc caa act ggc atg tac ggg gat tct ggt        3447
Val Glu Thr Thr Glu Asp Thr Gln Thr Gly Met Tyr Gly Asp Ser Gly
1070                1075                1080 tgt aaa acg gaa gtc gaa aat act aaa cta gta caa tcc ttc cac ttt        3495
Cys Lys Thr Glu Val Glu Asn Thr Lys Leu Val Gln Ser Phe His Phe
1085                1090                1095                1100 gat aac aag gaa cca gaa agt aac tct gag att cct aaa aaa gat aag        3543
Asp Asn Lys Glu Pro Glu Ser Asn Ser Glu Ile Pro Lys Lys Asp Lys
                1105                1110                1115 cca aag agt aat act agt tta cca gca act ggt gaa aac cac cat aat        3591
Pro Lys Ser Asn Thr Ser Leu Pro Ala Thr Gly Glu Asn His His Asn
         1120                1125                1130 atc ttc ttt tgg atg gtt act tct tgc tca ctt att agt agt gtt ttt        3639
Ile Phe Phe Trp Met Val Thr Ser Cys Ser Leu Ile Ser Ser Val Phe
1135                1140                1145 gta ata tca cta aaa tcc aaa aaa cgc cta tca tca tgt taa                3681
Val Ile Ser Leu Lys Ser Lys Lys Arg Leu Ser Ser Cys
         1150                1155                1160 aataagctgt tggtgac                                                     3698

<210> SEQ ID NO 2
<211> LENGTH: 1161
<212> TYPE: PRT
<213> ORGANISM: SFFBP gene

<400> SEQUENCE: 2

Met Thr Gln Lys Asn Ser Tyr Lys Leu Ser Phe Leu Leu Ser Leu Thr
 1               5                  10                  15

Gly Phe Ile Leu Gly Leu Leu Leu Val Phe Ile Gly Leu Ser Gly Val
                20                  25                  30

Ser Val Gly His Ala Glu Thr Arg Asn Gly Ala Asn Lys Gln Gly Ser
            35                  40                  45

Phe Glu Ile Lys Lys Val Asp Gln Asn Asn Lys Pro Leu Pro Gly Ala
        50                  55                  60

Thr Ser Ser Leu Thr Ser Lys Asp Gly Lys Gly Thr Ser Val Gln Ser
 65                  70                  75                  80

Phe Thr Ser Asn Asp Lys Gly Ile Val Asp Ala Gln Asn Leu Gln Pro
                85                  90                  95

Gly Thr Tyr Thr Leu Lys Glu Thr Ala Pro Asp Gly Tyr Asp Lys
            100                 105                 110

Thr Ser Arg Thr Trp Thr Val Thr Val Tyr Glu Asn Gly Tyr Thr Lys
        115                 120                 125

Leu Val Glu Asn Pro Tyr Asn Gly Glu Ile Ile Ser Lys Ala Gly Ser
    130                 135                 140

Lys Asp Val Ser Ser Ser Leu Gln Leu Glu Asn Pro Lys Met Ser Val
145                 150                 155                 160

Val Ser Lys Tyr Gly Lys Thr Val Ser Ser Gly Ala Ala Asp Phe
                165                 170                 175

Tyr Arg Asn His Ala Ala Tyr Phe Lys Met Ser Phe Glu Leu Lys Gln
            180                 185                 190

Lys Asp Lys Ser Glu Thr Ile Asn Pro Gly Asp Thr Phe Val Leu Gln
        195                 200                 205

Leu Asp Arg Arg Leu Asn Pro Lys Gly Ile Ser Gln Asp Ile Pro Lys
    210                 215                 220
```

-continued

```
Ile Ile Tyr Asp Ser Ala Asn Ser Pro Leu Ala Ile Gly Lys Tyr His
225                 230                 235                 240

Ala Glu Asn His Gln Leu Ile Tyr Thr Phe Thr Asp Tyr Ile Ala Gly
            245                 250                 255

Leu Asp Lys Val Gln Leu Ser Ala Glu Leu Ser Leu Phe Leu Glu Asn
            260                 265                 270

Lys Glu Val Leu Glu Asn Thr Ser Ile Ser Asn Phe Lys Ser Thr Ile
        275                 280                 285

Gly Gly Gln Glu Ile Thr Tyr Lys Gly Thr Val Asn Val Leu Tyr Gly
    290                 295                 300

Asn Glu Ser Thr Lys Glu Ser Asn Tyr Ile Thr Asn Gly Leu Ser Asn
305                 310                 315                 320

Val Gly Gly Ser Ile Glu Ser Tyr Asn Thr Glu Thr Gly Glu Phe Val
                325                 330                 335

Trp Tyr Val Tyr Val Asn Pro Asn Arg Thr Asn Ile Pro Tyr Ala Thr
            340                 345                 350

Met Asn Leu Trp Gly Phe Gly Arg Ala Arg Ser Asn Thr Ser Asp Leu
            355                 360                 365

Glu Asn Asp Ala Asn Thr Ser Ser Ala Glu Leu Gly Glu Ile Gln Val
    370                 375                 380

Tyr Glu Val Pro Glu Gly Glu Lys Leu Pro Ser Ser Tyr Gly Val Asp
385                 390                 395                 400

Val Thr Lys Leu Thr Leu Arg Thr Asp Ile Thr Ala Gly Leu Gly Asn
                405                 410                 415

Gly Phe Gln Met Thr Lys Arg Gln Arg Ile Asp Phe Gly Asn Asn Ile
            420                 425                 430

Gln Asn Lys Ala Phe Ile Ile Lys Val Thr Gly Lys Thr Asp Gln Ser
    435                 440                 445

Gly Lys Pro Leu Val Val Gln Ser Asn Leu Ala Ser Phe Arg Gly Ala
    450                 455                 460

Ser Glu Tyr Ala Ala Phe Thr Pro Val Gly Gly Asn Val Tyr Phe Gln
465                 470                 475                 480

Asn Glu Ile Ala Leu Ser Pro Ser Lys Gly Ser Gly Ser Gly Lys Ser
                485                 490                 495

Glu Phe Thr Lys Pro Ser Ile Thr Val Ala Asn Leu Lys Arg Val Ala
            500                 505                 510

Gln Leu Arg Phe Lys Lys Met Ser Thr Asp Asn Val Pro Leu Pro Glu
    515                 520                 525

Ala Ala Phe Glu Leu Arg Ser Ser Asn Gly Asn Ser Gln Lys Leu Glu
    530                 535                 540

Ala Ser Ser Asn Thr Gln Gly Glu Val His Phe Lys Asp Leu Thr Ser
545                 550                 555                 560

Gly Thr Tyr Asp Leu Tyr Glu Thr Lys Ala Pro Lys Gly Tyr Gln Gln
                565                 570                 575

Val Thr Glu Lys Leu Ala Thr Val Thr Val Asp Thr Thr Lys Pro Ala
            580                 585                 590

Glu Glu Met Val Thr Trp Gly Ser Pro His Ser Ser Val Lys Val Glu
    595                 600                 605

Ala Asn Lys Glu Val Thr Ile Val Asn His Lys Glu Thr Leu Thr Phe
    610                 615                 620

Ser Gly Lys Lys Ile Trp Glu Asn Asp Arg Pro Asp Gln Arg Pro Ala
625                 630                 635                 640

Lys Ile Gln Val Gln Leu Leu Gln Asn Gly Gln Lys Met Pro Asn Gln
```

-continued

```
                645                 650                 655
Ile Gln Glu Val Thr Lys Asp Asn Asp Trp Ser Tyr His Phe Lys Asp
                660                 665                 670
Leu Pro Lys Tyr Asp Ala Lys Asn Gln Glu Tyr Lys Tyr Ser Val Glu
                675                 680                 685
Glu Val Asn Val Pro Asp Gly Tyr Lys Val Ser Tyr Leu Gly Asn Asp
                690                 695                 700
Ile Phe Asn Thr Arg Glu Thr Glu Phe Val Phe Glu Gln Asn Asn Phe
705                 710                 715                 720
Asn Leu Glu Phe Gly Asn Ala Glu Ile Lys Gly Gln Ser Gly Ser Lys
                725                 730                 735
Ile Ile Asp Glu Asp Thr Leu Thr Ser Phe Lys Gly Lys Lys Ile Trp
                740                 745                 750
Lys Asn Asp Thr Ala Glu Asn Arg Pro Gln Ala Ile Gln Val Gln Leu
                755                 760                 765
Tyr Ala Asp Gly Val Ala Val Glu Gly Gln Thr Lys Phe Ile Ser Gly
                770                 775                 780
Ser Gly Asn Glu Trp Ser Phe Glu Phe Lys Asn Leu Lys Lys Tyr Asn
785                 790                 795                 800
Gly Thr Gly Asn Asp Ile Ile Tyr Ser Val Lys Glu Val Thr Val Pro
                805                 810                 815
Thr Gly Tyr Asp Val Thr Tyr Ser Ala Asn Asp Ile Ile Asn Thr Lys
                820                 825                 830
Arg Glu Val Ile Thr Gln Gln Gly Pro Lys Leu Glu Ile Glu Glu Thr
                835                 840                 845
Leu Pro Leu Glu Ser Gly Ala Ser Gly Gly Thr Thr Val Glu Asp
                850                 855                 860
Ser Arg Pro Val Asp Thr Leu Ser Gly Leu Ser Ser Glu Gln Gly Gln
865                 870                 875                 880
Ser Gly Asp Met Thr Ile Glu Glu Asp Ser Ala Thr His Ile Lys Phe
                885                 890                 895
Ser Lys Arg Asp Ile Asp Gly Lys Glu Leu Ala Gly Ala Thr Met Glu
                900                 905                 910
Leu Arg Asp Ser Ser Gly Lys Thr Ile Ser Thr Trp Ile Ser Asp Gly
                915                 920                 925
Gln Val Lys Asp Phe Tyr Leu Met Pro Gly Lys Tyr Thr Phe Val Glu
                930                 935                 940
Thr Ala Ala Pro Asp Gly Tyr Glu Ile Ala Thr Ala Ile Thr Phe Thr
945                 950                 955                 960
Val Asn Glu Gln Gly Gln Val Thr Val Asn Gly Lys Ala Thr Lys Gly
                965                 970                 975
Asp Thr His Ile Val Met Val Asp Ala Tyr Lys Pro Thr Lys Gly Ser
                980                 985                 990
Gly Gln Val Ile Asp Ile Glu Glu Lys Leu Pro Asp Glu Gln Gly His
                995                 1000                1005
Ser Gly Ser Thr Thr Glu Ile Glu Asp Ser Lys Ser Ser Asp Leu Ile
     1010                1015                1020
Ile Gly Gly Gln Gly Glu Val Val Asp Thr Thr Glu Asp Thr Gln Ser
1025                1030                1035                1040
Gly Met Thr Gly His Ser Gly Ser Thr Thr Glu Ile Glu Asp Ser Lys
                1045                1050                1055
Ser Ser Asp Val Ile Ile Gly Gly Gln Gly Gln Val Val Glu Thr Thr
                1060                1065                1070
```

-continued

```
Glu Asp Thr Gln Thr Gly Met Tyr Gly Asp Ser Gly Cys Lys Thr Glu
        1075            1080            1085

Val Glu Asn Thr Lys Leu Val Gln Ser Phe His Phe Asp Asn Lys Glu
    1090            1095            1100

Pro Glu Ser Asn Ser Glu Ile Pro Lys Lys Asp Lys Pro Lys Ser Asn
1105                1110            1115                1120

Thr Ser Leu Pro Ala Thr Gly Glu Asn His His Asn Ile Phe Phe Trp
            1125            1130                1135

Met Val Thr Ser Cys Ser Leu Ile Ser Ser Val Phe Val Ile Ser Leu
        1140            1145            1150

Lys Ser Lys Lys Arg Leu Ser Ser Cys
        1155            1160
```